US012605339B2

(12) United States Patent
Ozmen

(10) Patent No.: US 12,605,339 B2
(45) Date of Patent: Apr. 21, 2026

(54) METHOD FOR CARRYING BIOACTIVE MOLECULES USING NANOCARRIERS

(71) Applicant: Zekeriya Ozmen, Battalgazi/Malatya (TR)

(72) Inventor: Zekeriya Ozmen, Battalgazi/Malatya (TR)

( * ) Notice: Subject to any disclaimer, the term of this patent is extended or adjusted under 35 U.S.C. 154(b) by 705 days.

(21) Appl. No.: 17/921,308

(22) PCT Filed: Apr. 28, 2021

(86) PCT No.: PCT/TR2021/050402
§ 371 (c)(1),
(2) Date: Oct. 25, 2022

(87) PCT Pub. No.: WO2021/225548
PCT Pub. Date: Nov. 11, 2021

(65) Prior Publication Data
US 2023/0172860 A1 Jun. 8, 2023

(30) Foreign Application Priority Data
May 7, 2020 (TR) .................................. 2020/07135

(51) Int. Cl.
*A61K 9/16* (2006.01)
*A61K 31/121* (2006.01)
*A61K 36/71* (2006.01)

(52) U.S. Cl.
CPC .......... *A61K 9/1694* (2013.01); *A61K 9/1611* (2013.01); *A61K 31/121* (2013.01); *A61K 36/71* (2013.01)

(58) Field of Classification Search
None
See application file for complete search history.

(56) References Cited

FOREIGN PATENT DOCUMENTS

| | | |
|---|---|---|
| CN | 103860587 A | 6/2014 |
| CN | 105749287 A | 7/2016 |
| KR | 20040020328 A | 3/2004 |
| TR | 201711955 A2 | 11/2017 |
| TR | 201711955 A1 * | 3/2021 |
| WO | 2018046591 A1 | 3/2018 |

OTHER PUBLICATIONS

Muhtasib et al. (The medicinal potential of black seed (*Nigella sativa*) and its components, Advances in Phytomedicine, vol. 2, 2006, pp. 133-153).*
Written Opinion for corresponding PCT application No. PCT/TR2021/050402, mailed Aug. 31, 2021.
International Search Report for corresponding PCT application No. PCT/TR2021/050402, mailed Sep. 27, 2021.
Response to International Search Report under Article 34 for corresponding PCT/TR2021/050402, dated Mar. 2, 2022.

* cited by examiner

*Primary Examiner* — Melissa S Mercier
(74) *Attorney, Agent, or Firm* — Notaro, Michalos & Zaccaria P.C.

(57) ABSTRACT

The production method for absorbing at least one composition in the intestine with a high amount so that it is carried to the target tissues in a healthy way, wherein the composition contains at least one bioactive molecule and at least one carrier, has the steps of reducing the carrier to the nanosize, preparing the bioactive molecule so that it can be loaded on the nano-sized carrier, and loading the prepared bioactive molecule onto the nano-sized carrier is disclosed. Many bioactive molecules, especially curcumin, can be carried to target tissues in the living organism by using a nanocarrier. It can also be used in all sectors for carrying molecular structures at nanosize.

27 Claims, No Drawings

METHOD FOR CARRYING BIOACTIVE MOLECULES USING NANOCARRIERS

TECHNICAL FIELD

The present invention relates to a method for obtaining compositions enabling bioactive molecules to be carried to target tissues using a nanocarrier in a more economical, more efficient manner, with a higher amount.

BACKGROUND OF THE INVENTION

Clay, found in nature, has been frequently used in medical treatments (poisoning, detoxification treatments, wound healing, skin diseases and digestive system diseases) throughout human history.

Recently, with the rapid developments in nanotechnology, it has been revealed that clays can be used for carrying biomolecules and in the production of biomaterials. Clay minerals such as Halloysite and Attapulgite are frequently used inorganic materials. These clay minerals, namely aluminum-magnesium hydrosilicate (Al Mg-SiO$_2$·nH$_2$O), are currently used extensively in the field of medicine and pharmacology due to their layered structure, large surface area and highly variable cation capacity. In recent years, crystalline kaolinite, sepiolite and smectite (montmorillonite) group clays, which can easily be layered by physical methods such as mechanical mixing, centrifugation and decantation, are used to form nanoparticles.

According to the present invention, montmorillonite mineral known commercially as Bentonite, which is one of the clays that can be reduced to nanosize, is used as a nanocarrier.

Currently, bentonite clay can be reduced to nanosize and used as a bioactive molecule carrier. However, among the techniques used for reducing clay to nanosize, the method of grinding dry clay is very costly, while efficiency of the method of precipitating the clay via bubbling in water and separating the slurry is very low. Even though better efficiency is obtained by the methods that reduce clay to nanosize using simple centrifuge methods, about ⅓ of the clay is still wasted and it can only be reduced up to 100 nm.

When examining the techniques using clay as a bioactive molecule carrier system, many deficiencies and application errors are observed. Most practitioners use clays without reducing them to nanosize, and bioactive molecule carrier applications with micro-sized clays do not provide satisfying results.

In the Chinese Patent application titled "Curcumin-montmorillonite composition" with publication number CN103860587 (A), the clay could only be reduced to micro size, and resulting product was patented as a digestive system relaxant after alcohol consumption since absorption and bioavailability of the product is low.

In another study (Dong and Feng et al. 2005), anti-cancer drug paclitaxel molecules were loaded into a nanocarrier prepared with polylactic co-glycolic acid and montmorillonite having amphiphilic properties, and polyvinyl alcohol polymer was used for the exfoliation of clay. However, the desired treatment success could not be achieved with the nanocarrier obtained (its average size was measured as 305 nm) because the space between endothelial cells forming the wall of blood vessels in the tumor region is not more than 200 nm, although it is wider than its counterparts in healthy tissues. A 305 nm nanocarrier could not reach the tumor region in sufficient amount, which negatively affected treatment success. For a successful treatment, size of the nanocarrier is required be below 200 nm, and bioactive molecules carried by the nanocarrier must be carried up to the target tissue without leaking. Many practitioners capable of reducing clays down to 200 nm have used organic solvents to load the hydrophobic molecules into the nanocarrier obtained, but they have not been able to completely remove the organic solvents from the resultant product. Organic solvents are toxic when taken into the body. Therefore, practitioners had to apply a long centrifugation process to the resultant product in order to evaporate the organic solvent used in the mixture, and this long centrifugation process resulted in the release of biomolecule that had been previously loaded on the nanocarrier such that the amount of biomolecules loaded on the nanocarrier decreased. In addition, since some of the organic solvent penetrates into the clay, it cannot be removed from the medium despite long centrifugation processes.

In the Chinese patent application titled "Montmorillonite inlaid liposome preparation and preparation method thereof" with publication number CN105749287 (A), montmorillonite is used as a nanocarrier for a drug used as eye drops; however, since the organic solvent could not be removed from the product, it caused harm in its use for medical purposes, and thus, the product was not widely used for treatment of eye diseases.

In the Turkish patent application titled "Bioactive Component Release Nanocomposite Production Method" with publication number TR 2017/11955, the nanocarrier is obtained by centrifuge and homogenization methods. A process is disclosed in said patent application, in which clay is stirred with water at 3000 rpm in a homogenizer for 6 hours without interruption. The process causes deterioration in natural structure of the montmorillonite minerals in the clay, and reduces efficiency of obtaining nanocarrier. Long-term stirring at high speed deteriorates the natural structure of the nanocarrier, while mixing at very low speed is insufficient to reduce the clay to nanosize. Stirring at medium speed does not deteriorate the natural structure of the clay so that it provides a high efficiency nanocarrier. As a result, in the aforementioned patent application, the bubbling and decomposition of the clay is insufficient due to the revolution speeds or stirring and resting times used, and the efficiency of obtaining nanocarrier is low. In addition, the method used involves a centrifugation process in order to separate the bubbled clay layers and obtain a nanocarrier. However, said process results in obtaining a low-efficient nanocarrier with a deteriorated natural structure. Moreover, in said patent application, there is provided a process of dissolving glyceryl monostearate in water, pouring it into the prepared clay and stirring it in a homogenizer at 19700 rpm between 30 minutes and 6 hours. Due to the high stirring speed, the natural integrity of the nanocarrier is deteriorated. Efficiency is also reduced due to the fact that an additive is loaded into the nanocarrier before the bioactive molecule. Hydrophilic and hydrophobic bioactive molecules can be loaded into the nanocarrier obtained by the method used in the patent application. However, the bioactive molecule cannot be carried effectively to target tissues due to the lack of a strong bond between the nanocarrier and the bioactive molecule. Rapid release of the bioactive molecule before reaching the target tissues can also cause toxicity. Furthermore, since no water is added to the product obtained, its shelf life is very short. Addition of a preservative is required to extend the shelf life, which reduces the efficiency in the process of loading bioactive material into the nanocarrier.

BRIEF DESCRIPTION OF THE INVENTION

A production method according to the present invention for absorbing at least one composition in the intestine with a high amount so that it is carried to the target tissues in a healthy way, wherein the composition contains at least one bioactive molecule and at least one carrier, the production method comprising the steps of:

Reducing the carrier to the nanosize;

Preparing the bioactive molecule such that it can be loaded on the nano-sized carrier; and Loading the prepared bioactive molecule onto the nano-sized carrier;

wherein the step of reducing the carrier to the nanosize comprises the sub-steps of:

Adding a second amount of said carrier to a first amount of solvent to obtain a first mixture;

Stirring the first mixture for a first period at a rotational speed between 6500-7500 rpm;

Holding the mixture for a second period after the first period has completed;

Filtering the first mixture, which has been held for the second period, after the second period is completed;

Placing the filtered first mixture to a pressure vessel and subjecting it to a heat treatment applied by supplying heat under pressure in a closed manner for a third period;

Cooling the first mixture to a first temperature after said heat treatment;

Holding the cooled first mixture for a fourth period at a second temperature between 0 to −24° C.;

Holding the first mixture, which has been held for the fourth period, at the first temperature for a fifth period after the fourth period is completed;

Subjecting the first mixture, which has been held for the fifth period, to a second stirring process, after the fifth period is completed, for a sixth period at a rotational speed between 1000-2000 rpm, and resting the first mixture for a seventh period following the sixth period;

Repeating the second stirring process and the resting process for a certain period in a cycle, wherein the second stirring process is performed for the sixth period and the resting process is performed for the seventh period;

Resting the first mixture when the cycle is completed, and then, performing a filtering process thereof;

wherein the step of preparing the bioactive molecule such that it can be loaded on the nano-sized carrier comprises the sub-step of:

Adding a second amount of bioactive molecules to a first amount of amphiphilic excipient to obtain a second water-soluble mixture;

wherein the step of loading the prepared bioactive molecule onto the nano-sized carrier comprises the sub-steps of:

Adding water to the first mixture, which has been rested for the eighth period and then filtered, until the total volume becomes 1 liter;

Adding a third amount of the second mixture to the first mixture mixed with water to obtain a third mixture;

Adding a fourth amount of carbonate and a fifth amount of rock salt to the obtained third mixture, thereby obtaining a fourth mixture;

Subjecting the fourth mixture to a third stirring process for a ninth period at a certain period, and resting it for a tenth period after the ninth period;

Adding a sixth amount of water to the mixture obtained;

Leaving the prepared mixture to infuse;

Obtaining the composition once the infusion process is completed.

Thanks to the present invention, bioactive molecules can be absorbed in intestine up to 100% between the nanoparticle layers in carrier clays found in nature, and enter the blood so that they act at the cellular level without altering. Thanks to the production method of the composition according to the present invention, it is ensured that the bioactive molecules reach the target organ by using, in particular, clay (preferably montmorillonite mineral-bentonite clay) as a carrier. In addition, thanks to the production method of the invention (by freezing and re-thawing the aqueous solution in the developed method), the process of reducing the carrier to nanosize can be performed with much higher efficiency at much lower cost while obtaining a nanocarrier with better efficiency, which is much smaller than the applications included in the prior art (for example 100 nm and below). Therefore, the bioactive molecule can be absorbed with a high amount in the intestine in the nanocarrier, pass into the circulatory system without being eliminated in the liver, and reach the target tissues easily at an effective dose. Furthermore, rock salt and sodium bicarbonate used in the method increase the interaction of the bioactive molecule with the nanocarrier (montmorillonite), provide stronger bonds, increase the amount of bioactive molecule carried in the nanocarrier, and enable the bioactive molecule to be carried by the nanocarrier to the target tissues in an effective dose without leaking. Thus, the compositions obtained by said method can be used in treatment of many diseases, including cancer, directly alone or in combination with other therapeutic drugs or simultaneously with other drugs as part of a treatment method.

OBJECT OF THE INVENTION

An object of the present invention is to provide a production method for obtaining compositions enabling bioactive molecules to be carried to target tissues using a nanocarrier in a more economical, more efficient manner, with a higher amount.

Another object of the present invention is to provide a production method for obtaining compositions that enable bioactive molecules, especially curcumin, to be highly absorbed in the intestine, pass into the circulatory system without being eliminated at the liver and reach all cells in the body by using a nanocarrier, especially clay.

A further object of the invention is to provide a production method for obtaining compositions that enable bioactive molecules to reach the target organ by extending their half-life using nanocarrier.

Another object of the invention is to provide a production method for obtaining compositions for use in the treatment of various diseases, especially cancer diseases by carrying bioactive molecules to the target organ by using a nanocarrier.

Yet another object of the present invention is to provide a production method that will provide a stronger therapeutic effect from bioactive molecules while at the same time providing less side effects.

An object of the present invention is to provide a production method for achieving a more effective treatment using less bioactive molecules.

Yet a further object of the invention is to provide a production method for obtaining compositions that enable bioactive molecules to be highly absorbed in the intestine and reach the target organ using a nanocarrier.

DESCRIPTION OF THE INVENTION

Clay, found in nature, has been frequently used in medical treatments (poisoning, detoxification treatments, wound healing, skin diseases and digestive system diseases) throughout human history. Clay minerals such as Halloysite and Attapulgite are frequently used inorganic materials. These clay minerals, namely aluminum-magnesium hydrosilicate (Al Mg-SiO$_2$·nH$_2$O), are currently used extensively in the field of medicine and pharmacology due to their layered structure, large surface area and highly variable cation capacity. Crystalline kaolinite, sepiolite and smectite (montmorillonite) group clays that can easily form layers are used to form nanoparticles. Therefore, with the recent developments in nano-technology, clays can be used effectively for carrying biomolecules and producing biomaterials.

Curcumin is the most important component among the major bioactive components obtained from Rhizoma Curcumae of *Curcuma longa* plant, which is a yellow-flowered, large-leaved, perennial herbaceous plant genus belonging to the Zingiberaceae family. Curcumin is used in the conventional medicine for the treatment of various diseases such as indigestion, urinary system infections, liver diseases and rheumatoid arthritis. (Cooper, T. H., Clark, J. G., Guzinski, J. A. (1994). *In food phytochemicals for cancer prevention II: ACS Symposium Series*; Ho, C.-T., Ed.; *American Chemical Society: New York*, 547, pp 231-236). However, according to the studies regarding solvent-used forms of curcuma, it is concluded that 85% of curcuma is generally insoluble in the human body. For the remaining 15%, it is seen that the active ingredients in curcuma are not released. There is no benefit in consuming high amounts of curcuma or consuming curcuma in the form of pills or capsules in order to benefit from the active ingredients in curcuma. Therefore, liquid extract of curcuma is formed by developing the phase 3-A method. Here, with the use of curcuma extract, capacity to benefit from the active ingredients in curcuma is increased to 90%. In this way, consuming a single scale of curcuma extract (5 ml) is more beneficial than consuming 10 scales of curcuma powder. It is almost impossible to obtain curcuminoids found in one scale of extract by consuming curcuma powder. However, while the curcumin has been proven to be effective in many studies, it cannot be absorbed sufficiently in the intestine and its anti-inflammatory and anti-oxidant properties cannot be used due to its very short half-life. This poses a major obstacle to the widespread use of curcumin in medical treatment. However, use of curcumin in combination with carrier clays found in nature increases absorption of curcumin in the intestine and extends the half-life thereof. In this context, the present invention provides a production method for obtaining compositions enabling bioactive molecules, such as curcumin, to be carried to target tissues using a nanocarrier in a more economical, more efficient manner, with a higher amount.

The production method according to the present invention for absorbing at least one composition in the intestine with a higher amount so that it is carried to the target tissues in a healthy way, wherein the composition contains at least one bioactive molecule, preferably and in particular curcumin (1,7-bis(4-hidroksi-3-metoksifenil)-1,6-hep-tadien-3,5-dion), and at least one carrier, preferably and in particular clay (especially montmorillonite mineral-Bentonite clay), comprises the steps of: reducing the carrier to the nanosize; preparing the bioactive molecule such that it can be loaded on the nano-sized carrier; and loading the prepared bioactive molecule onto the nano-sized carrier. The step of reducing the carrier to the nanosized, which is included in the method, comprises the sub-steps of:

Adding a second amount of said carrier (preferably between 75-125 g, in particular substantially 100 g) to a first amount of solvent (e.g. 1 liter of water) to obtain a first mixture;

Stirring the first mixture obtained for a first period (preferably between 35-45 minutes, in particular substantially 40 minutes) at a rotational speed between 6500-7500 rpm (preferably at a rotational speed substantially of 7000 rpm);

Holding the mixture for a second period (preferably between 45 to 75 minutes, in particular substantially 60 minutes) after the first period has completed;

Filtering the first mixture, which has been held for the second period, after the second period is completed (e.g. by a fine-mesh filter with a mesh size preferably between 400 and 600 microns, more preferably 500 microns);

Placing the filtered first mixture to a pressure vessel and subjecting it to a heat treatment (boiling) applied by supplying heat under pressure in a closed manner for a third period (preferably 45 to 75 minutes, more preferably 60 minutes);

Cooling the first mixture to a first temperature, preferably between 20 to 25° C., after said heat treatment;

Holding the cooled first mixture for a fourth period (preferably, 24 hours) at a second temperature between 0 to −24° C.;

Holding the first mixture, which has been held for the fourth period, at the first temperature for a fifth period (preferably 12 hours) after the fourth period is completed;

Subjecting the first mixture, which has been held for the fifth period, to a second stirring process, after the fifth period is completed, for a sixth period (preferably 15-25 minutes, in particular substantially 20 minutes) at a rotational speed between 1000-2000 rpm (preferably at a rotational speed of substantially 1400 rpm), and resting the first mixture for a seventh period (preferably 35-45 minutes, in particular substantially 40 minutes) following the sixth period;

Repeating the second stirring process and the resting process for a certain period (e.g. 24 hours×14 days) in a cycle, wherein the second stirring process is performed for the sixth period and the resting process is performed for the seventh period;

When the cycle is completed, resting the first mixture preferably for an eighth period (e.g. a couple of hours) and then, performing a filtering process thereof.

The step of preparing the bioactive molecule such that it can be loaded on the nano-sized carrier, which is included in the method, comprises the sub-step of:

Adding a second amount of bioactive molecules (preferably up to 10% by weight of the total) to a first amount of amphiphilic excipient (preferably up to 90% by weight of the total) (preferably, the excipient contains emulsifier, in particular polysorbate 80, etc.) to obtain a second water-soluble mixture preferably in a liquid form.

The step of loading the prepared bioactive molecule onto the nano-sized carrier, which is included in the method, comprises the sub-steps of:

Adding water to the first mixture, which has been rested for the eighth period and then filtered, until the total volume becomes 1 liter;

Adding a third amount of the second mixture (preferably, 33 ml) to the first mixture mixed with water to obtain a third mixture;

Adding a fourth amount of carbonate (preferably 0.01%-0.04% sodium bicarbonate by weight of the total, more preferably 0.02% by weight of the total) and a fifth amount of rock salt (preferably 0.005%-0.02% by weight of the total, more preferably 0.01% by weight of the total) to the obtained third mixture, thereby obtaining a fourth mixture;

Subjecting the fourth mixture to a third stirring process for a ninth period (preferably 15-25 min, in particular substantially 20 min) at a certain period (preferably every 1 hour), preferably at a rotational speed of 1000-2000 rpm (preferably at a rotational speed of substantially 1400 rpm), and resting it for a tenth period (preferably 35-45 min, in particular substantially 40 min) after the ninth period;

Adding a sixth amount of water (preferably between 800-850 ml, especially 833 ml) to the mixture obtained;

Leaving the prepared mixture to infuse (preferably substantially for 48 hours);

Obtaining the composition once the infusion process is completed.

In an alternative embodiment of the present invention, in case the excipient contains polysorbate80 in the step of preparing the bioactive molecule such that it can be loaded onto the carrier, foam formation occurs after the process of resting the bioactive molecule for the tenth period in the step of loading the bioactive molecule to the nano-sized carrier. Therefore, the present invention comprises the steps of adding preferably 800-850 ml, more preferably 833 ml of water to remove the resulting foam, and infusing the prepared mixture preferably for 48 hours.

In an alternative embodiment of the present invention, said method comprises the step of adding a second bioactive molecule. Said second bioactive molecule is preferably added in the third stirring process after 4 hours. Said second bioactive molecule preferably comprises plant extracts (such as black seed oil in liquid form and/or black seed powder, oregano juice, carvacol molecule, thymokine molecule).

In the production method according to the present invention, a clay, especially the Montmorillonite mineral known commercially as Bentonite, which can be reduced to the nano-scale, is used as the carrier.

In the literature, the amount of water-soluble carrier is 4% to 9%, especially when bentonite clay is used. However, 9-10% of the carrier can be dissolved thanks to the production method according to the present invention. In the method of the present invention, a filtering process performed after a high-speed first stirring process causes removal of the precipitation generated during the first stirring process; then, the obtained liquid mixture is boiled to purify possible microbes; and after that, the solvent (e.g. water) molecules entering between the carrier (montmorillonite-bentonite clay) layers are crystallized by a holding process performed at a second temperature between 0 to −4° C. (it can also be held at a temperature between −18 and −24° C. to shorten the waiting time) so that the layers are separated thoroughly. In other words, e.g. by freezing the aqueous solution of clay to be used as a carrier, the water molecules crystallizing between the clay layers provide better separation of the clay layers and the formation of smaller particles. Efficiency of the nano-sized clay obtained by the method of the present invention is much higher than the clays used in the known-art. The second stirring process performed afterwards at a lower speed provides size reduction without deteriorating the natural structure, and the carrier (montmorillonite-bentonite clay) that absorbs water molecules in each resting process performed after each second stirring process is repeatedly reduced. Thus, the size of the carrier can be reduced to less than 100 nm.

Since curcumin is a water-insoluble molecule, it is used by dissolving in organic solvents such as acetone and alcohol in the known-art. However, in such uses, organic solvents cannot be completely removed from the medium such that the composition containing curcumin is toxic. According to the present invention, amphiphilic excipients, which are preferably suitable for the food codex, and more preferably emulsifiers suitable for the food codex are used in order to dissolve curcumin. Thus, it can be ensured that compositions containing curcumin are not toxic. However, while using curcumin with an emulsifier, the desired amount of curcumin that can be loaded into the nanocarrier cannot be provided with the known-art techniques. Moreover, in these techniques, the amount of curcumin decreases even more until it reaches the target tissues, since the curcumin cannot be firmly adsorbed to the nanocarrier. According to the known-art techniques, up to 1250 micrograms of curcumin can be carried in 1 ml of montmorillonite (122 nm) solution, of which 812 micrograms can be carried in the nanocarrier (montmorillonite) and the remaining part can be carried on the carrier surface. Since the curcumin carried on the nanocarrier surface cannot reach the target tissues, a maximum of 812 micrograms of curcumin can be effectively carried to the target tissues in these techniques. However, thanks to the method of the present invention, the amount of curcumin loaded into the nano-sized carrier is appropriately higher, and the curcumin can adhere to carrier more firmly. For example, in an embodiment of the invention, 1980 micrograms of curcumin can be carried in 1 ml of carrier. At least 1485 micrograms of curcumin can be carried effectively in 1 ml of montmorillonite solution.

The rock salt used in the production method according to the present invention preferably has a pH value of 8-8.5 at 25° C. In addition, the specific conductivity of the rock salt at 25° C. is preferably 1900 mho/cm. In addition, the evaporation residue of the rock salt at 180° C. is preferably 3700 mg/lt. The rock salt preferably contains 70 mg/l of potassium, 2580 mg/l of sodium, 550 mg/l of calcium, 4510 mg/l of magnesium, 7.6 mg/l of boron, 2.2 mg/l of lithium, 334 mg/l of $HCO_3$, 102 mg/l of $CO_3$, 23600 mg/l of $SO_4$, 960 mg/l of chlorine, 0.4 mg/l of fluorine, and 0.8 mg/l of $SO_2$. These elements/minerals allow the bioactive molecule (e.g. curcumin) to be better adsorbed to the nanocarrier (e.g. montmorillonite) by making both ionic and hydrogen bond interactions stronger. Also, a more alkaline medium is created by adding sodium bicarbonate.

In a preferred embodiment of the present invention, said natural clay preferably comprises smectite group clay. Said calcium bentonite clay is in liquid and drinkable form, which is now used as a food supplement. Drinkable calcium bentonite clay is mostly used to purify the body from toxic substances, heavy metals, radiation etc. accumulated in the body. Thus, the effectiveness of the composition can be increased by using natural clay, preferably comprising calcium bentonite clay.

In a preferred embodiment of the present invention, the composition obtained by the production method of the invention is used in the treatment of cancer types alone or in combination with other anti-cancer drugs due to its anti-carcinogenic effect. The cancer types may include, for example, cervical cancer, leukemia, esophageal cancer, brain tumor, spinal cord tumor, skin cancer, bladder cancer, pancreatic cancer, lung cancer, bone cancer, colorectal cancer, breast cancer, kidney cancer, prostate cancer, stomach cancer, etc.

In a preferred embodiment of the present invention, the composition obtained by the production method of the invention has anti-carcinogenic effects, as well as providing inflammation, cell proliferation, some oncogenes, tumor implantation and biotransformation of carcinogens, and suppressing transcription NF-kB and COX2 enzymes so as to activate the glutathione-s-transferase (GST) enzyme. Since the composition obtained by the production method of the invention utilizes almost 100% of the curcumin active ingredient, p53 protein is activated due to the chelator property of curcumin so that P53 affects cancerous cells. A decrease in cell proliferation and an increase in apoptosis is observed in patients for whom the composition obtained by the production method of the invention is used. In addition, a decrease in microvascular density is detected.

In another preferred embodiment of the invention, the composition obtained by the production method of the invention is used for patients with prostate cancer. Curcumin active ingredient inhibits development of prostate cancer and acts as a potent therapeutic anti-cancer agent in preventing development of this cancer in a hormone-resistant state.

In another preferred embodiment of the present invention, the composition obtained by the production method of the invention is used to prevent metastasis. While curcumin regulates cellular structure, it prevents cell fragmentation and negative cell signals. These features allow the composition to prevent metastasis.

In another preferred embodiment of the present invention, the composition obtained by the production method of the invention is used in the treatment of liver diseases, lung diseases, skin diseases, neurodegenerative disorders, heart diseases, skeletal and bone disorders, endocrine disorders and infectious diseases. Exemplary liver diseases may include alcohol-related liver diseases, fibrosis, cirrhosis and jaundice; and exemplary lung diseases may include Hyaline membrane disease, bronchitis and cystic fibrosis. Exemplary skin diseases may include scleroderma, psoriasis, eczema, scabies, parasitic skin diseases (scabies). Neurodegenerative disorders suitable for using the composition obtained by the production method of the invention may be exemplified as Parkinson's disease, Alzheimer's disease, multiple sclerosis, lewy body dementia and epilepsy; infectious diseases may be exemplified as measles, malaria, chickenpox, smallpox, chronic diarrhea, anthelmintic, leishmaniasis; endocrine disorders may be exemplified as diabetes and hypothyroidism; heart diseases may be exemplified as arteriosclerosis, heart attack and hypolipidemia; and skeletal and bone disorders may be exemplified as osteoporosis and Foncani anemia.

In another preferred embodiment of the invention, the composition obtained by the production method of the invention is used in leukemia-lymphoma, gastrointestinal system cancers, genitourinary system cancers, breast cancer, ovarian cancer, head and neck cancer, lung cancer, melanoma and neurological cancers. In Phase 1 clinical studies, it has been observed that curcumin obtained from curcuma is beneficial and safe for the future, as well as having a healing role especially for cancer types in which the cell cycle is disrupted. In these phase studies, the curcumin in the composition obtained by the production method has shown a therapeutic effect (curative treatment) against various diseases in humans. Curcumin in the composition obtained by the production method was found very useful in cancer, cardiovascular diseases, diabetes, arthritis and neurological diseases.

In a further embodiment of the invention, the composition obtained by the production method of the invention is preferably used in gastrointestinal system cancers and colorectal cancers.

In an alternative embodiment of the present invention, the composition obtained by the production method of the invention is used alone or in combination with chemotherapeutic agents or simultaneously with other therapeutic drugs as part of a treatment method. Curcumin is known to increase the death rate of cancer cells and prevent tumor cells from dividing. In addition, it has been determined that curcumin increases the effect of radiotherapy, so that it provides faster results from the treatment. Many studies have been published in the recent years, revealing that curcumin is effective in increasing the effectiveness of radiation or chemotherapeutic agents, which are widely used in cancer treatment, and in preventing normal tissue damage caused by the treatment. However, since absorption of curcumin active agent in the intestine is very low and its half-life is short, it cannot be utilized. Thanks to the present invention, it can be used to increase the effect of radiotherapy and increase the death rate of cancer cells since the composition obtained by the production method of the invention enables the curcumin active agent to be absorbed enough to be carried to the target organ, and the half-life thereof is increased. Chemotherapeutic drugs lead to accumulation of toxic substances in the body. Combining the composition obtained with the production method of the invention with chemotherapeutic agents also enables curcumin to remove harmful chemicals and toxins in the body such that detoxification is performed.

Thanks to the present invention, bioactive molecules can be absorbed in intestine up to 100% between the nanoparticle layers in carrier clays found in nature, and enter the blood so that they act at the cellular level without altering. Thanks to the production method of the composition according to the present invention, it is ensured that the bioactive molecules reach the target organ by using, in particular, clay (preferably montmorillonite mineral-bentonite clay) as a carrier. In addition, thanks to the production method of the invention (by freezing and re-thawing the aqueous solution in the developed method), the process of reducing the carrier to nanosize can be performed with much higher efficiency at much lower cost while obtaining a nanocarrier with better efficiency, which is much smaller than the applications included in the prior art (for example 100 nm and below). Therefore, the bioactive molecule can be absorbed with a higher amount in the intestine in the nanocarrier, pass into the circulatory system without being eliminated in the liver, and reach the target tissues easily at an effective dose. Furthermore, rock salt and sodium bicarbonate used in the method increase the interaction of the bioactive molecule with the nanocarrier (montmorillonite), provide stronger bonds, increase the amount of bioactive molecule carried in the nanocarrier, and enable the bioactive molecule to be carried by the nanocarrier to the target tissues in an effective dose without leaking. Thus, the compositions obtained by said method can be used in treatment of many diseases, including cancer, directly alone or in combination with other therapeutic drugs or simultaneously with other drugs as part of a treatment method.

The invention claimed is:

1. A production method for absorbing at least one composition in the intestine so that it is carried to the target tissues, wherein the composition contains at least one bioactive molecule and at least one carrier, the production method comprising the steps of:

reducing the carrier to the nanosize;

preparing the bioactive molecule such that it can be loaded on the nano-sized carrier; and loading the prepared bioactive molecule onto the nano-sized carrier;

characterized in that the step of reducing the carrier to the nanosize comprises the sub steps of:

adding a second amount of said carrier to a first amount of solvent to obtain a first mixture;

stirring the first mixture for a first period at a rotational speed between 6500-7500 rpm;

holding the first mixture for a second period after the first period has completed;

filtering the first mixture, which has been held for the second period, after the second period is completed;

placing the filtered first mixture to a pressure vessel and subjecting it to a heat treatment applied by supplying heat under pressure in a closed manner for a third period;

cooling the first mixture to a first temperature after said heat treatment;

holding the cooled first mixture for a fourth period at a second temperature between 0 to −24° C.;

holding the first mixture, which has been held for the fourth period, at the first temperature for a fifth period after the fourth period is completed;

subjecting the first mixture, which has been held for the fifth period, to a second stirring process, after the fifth period is completed, for a sixth period at a rotational speed between 1000-2000 rpm, and resting the first mixture for a seventh period following the sixth period;

repeating the second stirring process and the resting process for a certain period in a cycle, wherein the second stirring process is performed for the sixth period and the resting process is performed for the seventh period;

resting the first mixture when the cycle is completed, and then, performing a filtering process thereof;

that the step of preparing the bioactive molecule such that it can be loaded on the nano sized carrier comprises the sub-step of:

adding a second amount of bioactive molecules to a first amount of amphiphilic excipient to obtain a second water-soluble mixture;

that the step of loading the prepared bioactive molecule onto the nano-sized carrier comprises the sub-steps of:

adding water to the first mixture, which has been rested for the eighth period and then filtered, until the total volume becomes 1 liter;

adding a third amount of the second mixture to the first mixture mixed with water to obtain a third mixture;

adding a fourth amount of carbonate and a fifth amount of rock salt to the obtained third mixture, thereby obtaining a fourth mixture;

subjecting the fourth mixture to a third stirring process at a rotational speed of 1000-2000 rpm, between 15 to 25 minutes, wherein the said third stirring process is performed in every 1 hour, and after the third stirring process, resting the fourth mixture between 35 to 45 minutes;

adding a sixth amount of water to the mixture obtained;

leaving the prepared mixture to infuse; and obtaining the composition once the infusion process is completed.

2. The production method according to claim 1, characterized in that the first amount of solvent is 1 liter of water.

3. The production method according to claim 1, characterized in that the second amount of said carrier is between 75 to 125 gr.

4. The production method according to claim 1, characterized in that the first period is between 35 to 45 minutes.

5. The production method according to claim 1, characterized in that the second period is between 45 to 75 minutes.

6. The production method according to claim 1, characterized in that the third period is between 45 to 75 minutes.

7. The production method according to claim 1, characterized in that the heat treatment is a boiling process.

8. The production method according to claim 1, characterized in that the sixth period is between 15 to 25 minutes.

9. The production method according to claim 1, characterized in that the seventh period is between 35 to 45 minutes.

10. The production method according to claim 1, characterized in that the first temperature is between 20 to 25° C.

11. The production method according to claim 1, characterized in that the fourth period is 24 hours.

12. The production method according to claim 1, characterized in that the fifth period is 12 hours.

13. The production method according to claim 1, characterized in that the first amount of amphiphilic excipient is 90% by weight of the total.

14. The production method according to claim 1, characterized in that the second amount of bioactive molecules is 10% by weight of the total.

15. The production method according to claim 1, characterized in that the amphiphilic excipient is an emulsifier.

16. The production method according to claim 1, characterized in that the third amount of the second mixture is 33 ml.

17. A production method according to claim 1, characterized in that the fourth amount of carbonate is 0.02% by weight of the total.

18. The production method according to claim 1, characterized in that the fifth amount of rock salt is 0.01% by weight of the total.

19. The production method according to claim 1, characterized in that the sixth amount of water is between 800 to 850 ml.

20. The production method according to claim 1, characterized by comprising the step of adding a second bioactive molecule.

21. The production method according to claim 20, characterized in that the second bioactive molecule is added after 4 hours from the beginning of the third stirring process.

22. The production method according to claim 21, characterized in that the second bioactive molecule comprises plant extracts.

23. The production method according to claim 22, characterized in that the plant extracts comprise black seed oil in liquid form and/or black seed powder.

24. The production method according to claim 1, characterized in that the bioactive molecule is curcumin.

25. The production method according to claim 1, characterized in that the carrier is clay.

26. The production method according to claim 24, characterized in that the clay is montmorillonite mineral.

27. A composition prepared according to a production method defined in claim 1.

* * * * *